United States Patent

Grofcisk et al.

[11] Patent Number: 5,573,021
[45] Date of Patent: Nov. 12, 1996

[54] COMBINED FLOSSER AND FLOSS DISPENSER DEVICE

[75] Inventors: Deborah A. Grofcisk, Wilmington, Del.; John W. Dolan, Boothwyn, Pa.; John W. Spencer, Jr., Rising Sun, Md.

[73] Assignee: W. L. Gore & Associates, Inc., Newark, Del.

[21] Appl. No.: 383,335

[22] Filed: Feb. 3, 1995

[51] Int. Cl.⁶ .................................. A61C 15/00
[52] U.S. Cl. .............................. 132/324; 132/325
[58] Field of Search ........................... 132/323, 324, 132/325, 326, 327

[56] References Cited

U.S. PATENT DOCUMENTS

| | | | |
|---|---|---|---|
| D. 285,368 | 8/1986 | Morin et al. | D28/64 |
| D. 309,041 | 7/1990 | Schreider | D28/64 |
| D. 310,582 | 9/1990 | Kujirai | D28/64 |
| 788,947 | 5/1905 | Roth . | |
| 1,618,351 | 2/1927 | Raycraft | 132/324 |
| 2,354,454 | 7/1944 | Geffner | 132/323 |
| 3,533,420 | 10/1970 | Maloney et al. | 132/325 |
| 3,592,203 | 7/1971 | Johnson | 132/323 |
| 3,834,404 | 9/1974 | Chica | 132/323 |
| 3,882,879 | 5/1975 | Lucas | 132/326 |
| 3,913,597 | 10/1975 | Day | 132/92 R |
| 3,915,178 | 10/1975 | Zellers | 132/92 R |
| 3,949,769 | 4/1976 | Minka | 132/91 |
| 3,960,159 | 6/1976 | Tesberg | 132/90 |
| 4,005,721 | 2/1977 | Yasumoto | 132/91 |
| 4,008,728 | 2/1977 | Sanchez | 132/92 R |
| 4,014,354 | 3/1977 | Garrett | 132/90 |
| 4,016,892 | 4/1977 | Chodorow | 132/91 |
| 4,022,229 | 5/1977 | Minka | 132/92 R |
| 4,031,909 | 6/1977 | Kelley | 132/91 |
| 4,052,994 | 10/1977 | Thun | 132/92 R |
| 4,162,687 | 7/1979 | Lorch | 132/91 |
| 4,206,774 | 6/1980 | Griparis | 132/92 R |
| 4,522,216 | 6/1985 | Bunker | 132/92 R |
| 4,556,074 | 12/1985 | Morin et al. | 132/92 R |
| 4,655,233 | 4/1987 | Laughlin | 132/91 |
| 4,655,234 | 4/1987 | Bowden | 132/92 A |
| 4,671,307 | 6/1987 | Curbow et al. | 132/91 |
| 4,729,392 | 3/1988 | Tenny | 132/91 |
| 4,736,757 | 4/1988 | Badoux | 132/91 |
| 4,790,336 | 12/1988 | Kuo | 132/325 |
| 4,807,752 | 2/1989 | Chodorow | 206/63.5 |
| 4,830,032 | 5/1989 | Jousson | 132/323 |
| 4,883,080 | 11/1989 | Lang | 132/322 |
| 4,936,326 | 6/1990 | Eckroat | 132/326 |
| 4,966,176 | 10/1990 | Lachenberg | 132/325 |
| 5,060,681 | 10/1991 | Westbrook et al. | 132/325 |
| 5,127,415 | 7/1992 | Preciutti | 132/323 |
| 5,176,157 | 1/1993 | Mazza | 132/325 X |
| 5,188,133 | 2/1993 | Romanus | 132/325 |
| 5,197,498 | 3/1993 | Stewart | 132/325 |
| 5,253,662 | 10/1993 | Won | 132/325 |
| 5,279,314 | 1/1994 | Poulos et al. | 132/322 |
| 5,287,865 | 2/1994 | Fulton | 132/323 |
| 5,323,796 | 6/1994 | Urso | 132/322 |
| 5,411,041 | 5/1995 | Ritter | 132/323 X |

FOREIGN PATENT DOCUMENTS 0611533  8/1994  European Pat. Off. .

*Primary Examiner*—Nicholas D. Lucchesi
*Attorney, Agent, or Firm*—David J. Johns

[57] ABSTRACT

The present invention is an improved flosser device for holding and manipulating floss during flossing. The flosser employs a forked tine design for retaining the floss, whereby the floss is maintained in an orientation essentially perpendicular to the longitudinal axis of the handle of the flosser, but offsets the tines both onto one side of the handle to make it much easier to view the area being flossed. A slanted base is also provided to allow the flosser to be stored on end, with the tines kept away from contaminated surfaces.

16 Claims, 3 Drawing Sheets

U.S. Patent
Nov. 12, 1996
Sheet 1 of 3
5,573,021
FIG. 1
FIG. 2
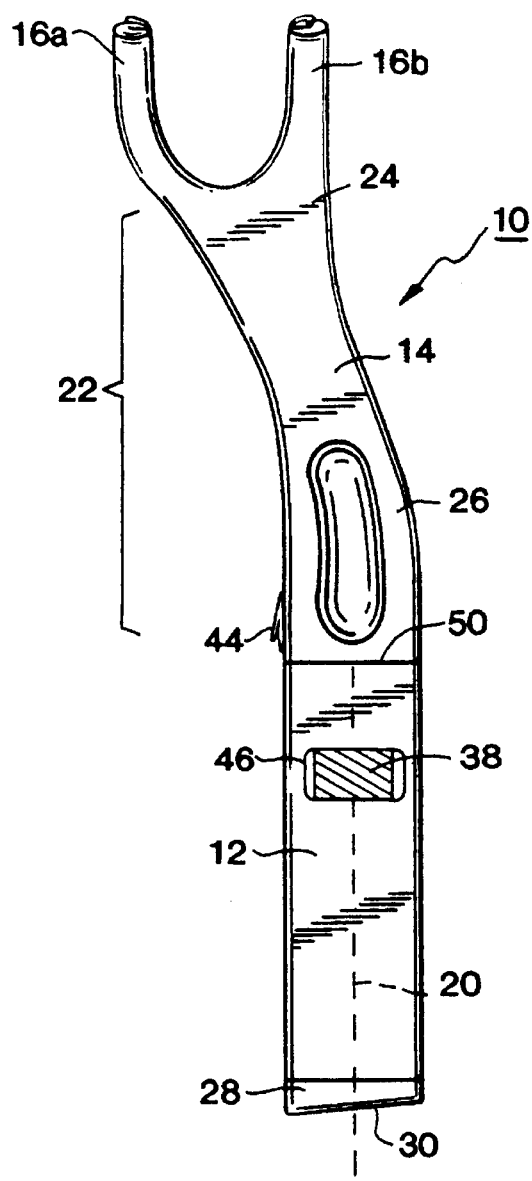
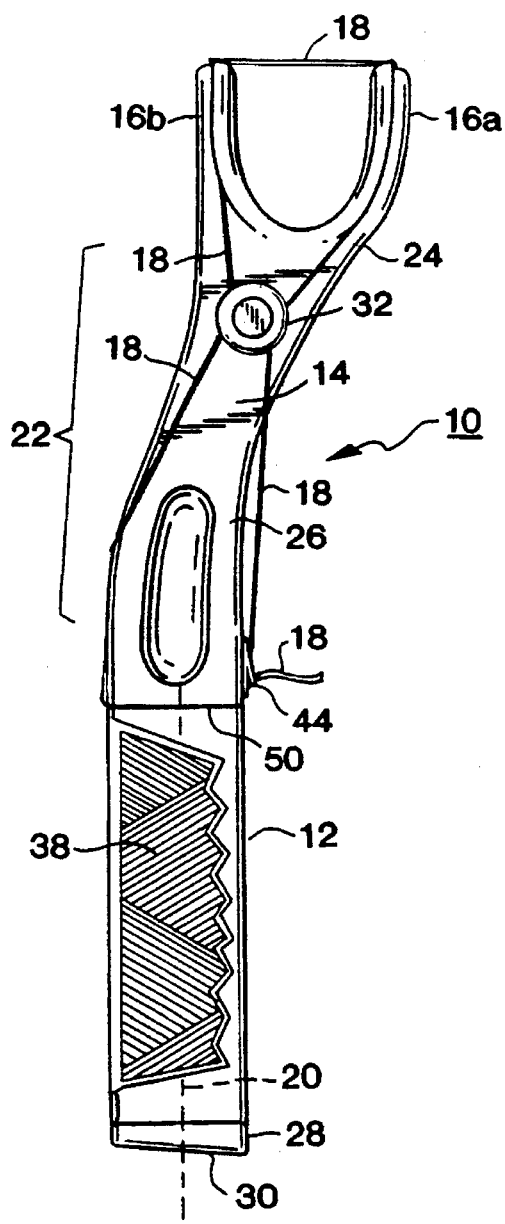

COMBINED FLOSSER AND FLOSS DISPENSER DEVICE

BACKGROUND OF THE INVENTION

1. Field of the Invention

The present invention relates to apparatus for holding, tensioning, and manipulating dental floss for use while flossing.

2. Description of Related Art

A number of dental floss holders have been invented which retain a strand of dental floss taut between some type of prongs or tines in order to permit the device to be used to manipulate dental floss between the teeth and move it back and forth for cleaning of the teeth. For example, U.S. Pat. Nos. 4,162,687 to Lorch, 4,655,233 to Laughlin, 4,736,757 to Badoux, 4,790,336 to Kuo, 5,188,133 to Romanus, and 5,197,498 to Stewart each discloses a dental floss holder that includes a "forked" end. This is a common and popular configuration for a flosser device, with the floss held in an orientation perpendicular to the longitudinal axis of the flosser. This form of perpendicular floss orientation is desirable in that the floss can be easily oriented between hard-to-reach back teeth when the floss is positioned parallel to the gap between the back teeth. The perpendicular orientation of the floss in the forked devices assists the user in aligning the floss for insertion within these gaps. Despite this advantage, many still find it difficult to position the floss using a forked flosser since the user's hand often blocks the view of the mouth while flossing with this tool.

Another approach to flossing is found in "sword" flosser devices that orient the floss parallel to or at a slant with the longitudinal axis of the flosser. Examples of these devices are found in U.S. Pat. Nos. 3,949,769 to Minka, 3,960,159 to Tesberg, 4,005,721 to Yasumoto, 4,031,909 to Kelley, 4,522,216 to Bunker, 4,556,074 to Morin et al., and 4,655,234 to Bowden, 4,729,392 to Tenny, and Des. 309,041 to Schreider. Due to the slant inherent in these devices, the user's hand tends to be positioned to a side, making it sometimes easier to view the area being flossed. Unfortunately, positioning of the floss between back teeth may be considerably harder with these blade devices due to difficult angle of attack to the gaps between back teeth when the floss is not positioned perpendicular to the handle of the flosser.

Another common concern with all kinds of flosser devices is how to easily install and anchor the floss prior to use. A number of interesting approaches have been proposed in this regard, including many different forms of threading and floss cutting devices. While some of these devices function adequately, it is believed that many of these devices are far too complex or difficult to use. The ease of threading the device is of particular interest with any kind of flosser device since flossers in general tend to be used by people who may already have manual dexterity problems. Another consideration in providing a threading mechanism is that hygiene issues demand that the mechanism be readily cleaned and that no used floss be left on the flosser after each use so as to avoid bacterial growth, odors, and other problems.

In many cases, an extended length of floss is positioned in the handle of the device to provide a self-contained unit whereby the floss can be easily replaced as needed. Again, this is usually done with some built-in means to thread and anchor the new floss, and cut and remove the old floss. While having floss built into the flosser itself is considered desirable, it tends to add to the bulk and complexity of the flosser. One of the problems with a flosser with a substantial supply of floss in its handle is that the flosser may be difficult to store since the flosser will not stand upright on its own. Another problem with flossers having a built-in supply of floss is that it is often difficult to judge the amount of floss remaining in the device at any given time. The weight of the flosser itself often belies the fact that the floss supply has diminished and may be in need of replacement.

Accordingly, it is a primary purpose of the present invention to provide a flosser device that has the ease of use of a "forked" flosser, with the floss oriented perpendicular to the longitudinal axis of the flosser, while not unnecessarily blocking the view of the teeth of the user during flossing.

It is another purpose of the present invention to provide a flosser device that has its own built-in floss supply yet is adapted to stand upright so as to occupy minimal shelf space and to avoid unwanted contamination.

These and other purposes of the present invention will become evident from review of the following specification.

SUMMARY OF THE INVENTION

The present invention comprises an improved "forked" dental flosser device for use in holding and manipulating floss during a flossing process. The flosser of the present invention employs forked tines that hold the floss substantially perpendicular to the longitudinal axis of the handle of the flosser. Unlike previous forked flossers, however, the flosser of the present invention has a transition segment with a double bend that offsets the tines both on one side of the longitudinal axis of the flosser to provide a clearer view around a user's hand to the area being flossed. This configuration of the flosser of the present invention retains all of the benefits of a forked flosser design while making it easier to view the area being flossed.

A further improvement in the flosser of the present invention is its use of an inclined or slanted base that allows the flosser to be stood upright on a counter or work table, or in a storage cabinet. The unique slanted base provides balance to maintain the flosser upright against the weight of the offset tines. Upright orientation of the flosser is considered particularly beneficial since it assures that the floss and the tines of the flosser are maintained away from surfaces that may contaminate or be contaminated by the flosser. Further, the upright orientation of the flosser makes it easier to store.

The preferred flosser of the present invention includes a built-in supply of floss in its handle and apparatus to thread, retain, and cut the floss. Most preferably, the flosser also includes means to readily monitor the amount of floss remaining in the flosser at any given time, such as a window in its side or base.

DESCRIPTION OF THE DRAWINGS

The operation of the present invention should become apparent from the following description when considered in conjunction with the accompanying drawings, in which:

FIG. 1 is a front elevation view of a floss holder of the present invention;

FIG. 2 is a back elevation view of the floss holder of the present invention, with a portion of its handle shown cut-away to expose a spool of floss contained therein;

DETAILED DESCRIPTION OF THE INVENTION

Figure 3:
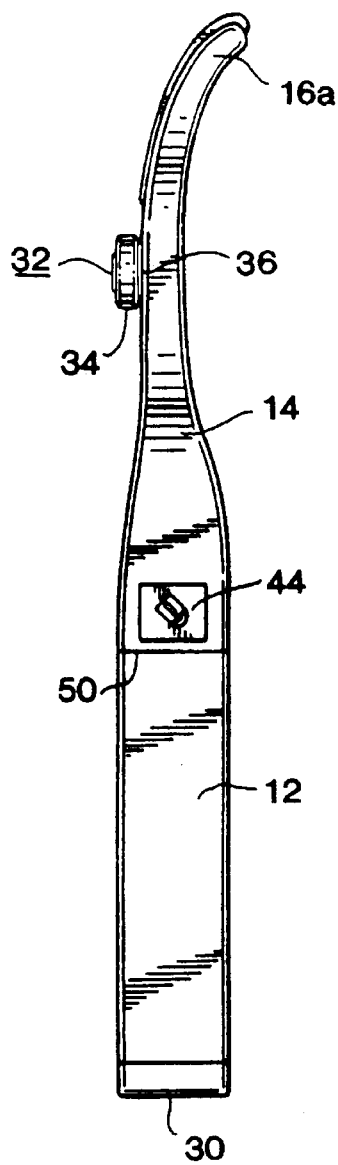
FIG. 3 is a left side elevation view of the floss holder of the present invention.
Figure 4:
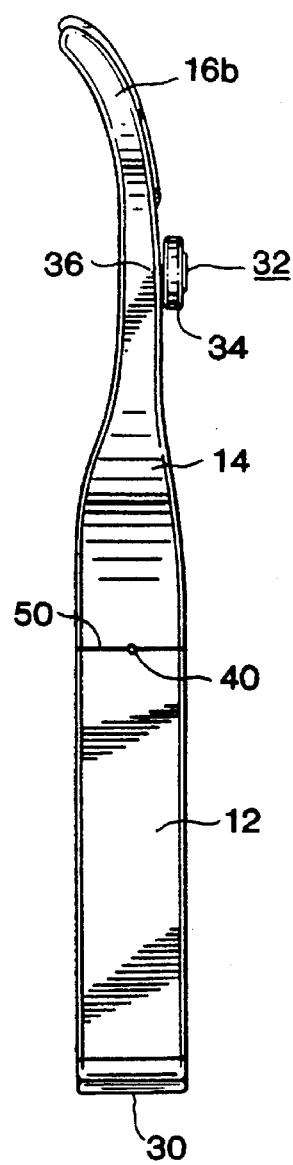
FIG. 4 is a right side elevation view of the floss holder of the present invention.
Figure 5:
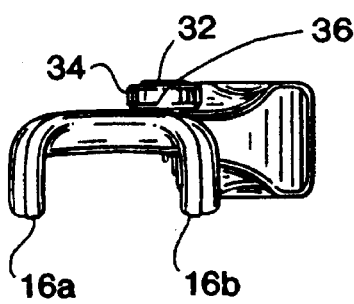
FIG. 5 is a top plan view of the floss holder of the present invention.

The present invention is an improved flosser device for use in holding and manipulating dental floss while a user is flossing teeth.

FIGS. 1 through 5 illustrate one embodiment of a flosser 10 of the present invention. The flosser 10 comprises a handle 12, a transition segment 14, and a pair of tines 16a, 16b. As can be seen, the tines are oriented in a "forked" configuration, positioning floss 18 extending between the tines 16 essentially perpendicular to a longitudinal axis 20 of the flosser 10. This configuration for a flosser is preferred over a "sword" design, where the floss is held parallel or at an intersecting angle to the longitudinal axis of the handle, since the floss can be more easily aligned and inserted between back teeth during flossing.

In order to avoid the previous problem of having the handle of the forked flosser obscuring the user's view of the mouth, the present invention employs the transition segment 14 to offset both of the tines to one side of the longitudinal axis 20 of the handle 12, as shown. This is accomplished by providing a double bend 22 in the transition segment 14, comprising a first bend 24 and a second bend 26. The double bend 22 acts to offset the tines 16 out of the axis of the handle while still assuring that the perpendicular forked tine configuration is maintained. It has been determined that by employing a double bend 22, the user of the flosser (i.e., either the person having his or her teeth flossed or a third person (e.g., a dental hygienist)) has a clearer view of the area being flossed without the handle and the user's hand obscuring the view. It should be appreciated that the double bend 22 of the present invention may take a variety of configurations without departing from the intent of the present invention. For instance, the double bend may be oriented in either a right handed configuration, as shown, or a mirror image left handed configuration. Further, the two bends may be arranged in virtually any of a number of different manners so long as the resulting flosser maintains a perpendicular "forked" floss orientation and the tines are offset to one side of the longitudinal axis of the handle.

A further improvement of the flosser of the present invention comprises its base 28 on its distal end 30. As can be best seen in FIGS. 1 and 2, the base 28 is slanted in a direction opposite that of the offset tines at an angle of 1 to 10 degrees off level. By providing a slanted base, the flosser 20 can be stood upright on its distal end 30, making it easier to store in less space and to keep the tines and floss away from surfaces that could spread contamination. The use of a flat, slanted base provides sufficient lean to the flosser when stood on end, shifting the flosser approximately 1 to 10 degrees off vertical, to assure sufficient balance that the flosser will not fall over in the direction of the offset tines. In the preferred embodiment shown, the flosser has an inclined base 5 degrees off level, which leans the flosser approximately 5 degrees off vertical when stood on end.

In order to assist in retaining the floss tautly between the tines in use, the flosser 10 should include some means to tightly grip the floss during use. Preferably, this grip means should be easily threaded and unthreaded by the user with minimal dexterity requirements. In the preferred embodiment of the present invention illustrated, the grip means comprises a single button 32 mounted on the flosser, ideally on the handle 12 or transition segment 14, around which the floss can be wrapped. As is shown in FIG. 2, the floss 18 can be easily wrapped around button 32, threaded through tines 16b and 16a, and again wrapped around the button 32 to establish a tight floss retention. As can be better seen in FIGS. 3 and 4, the button comprises an outer knob 34 attached to the flosser by a constricted stem 36. By attaching the knob 34 to the flosser 10 with a tapered, constricted connection between them, each end of the floss 18 can be retained in position through no more than one or two wraps around the stem 36 of the button 32. To change floss, the floss need only be unwrapped by pulling on a trailing piece of floss and then removed.

A particularly desirable feature of the flosser of the present invention is that a substantial floss supply 38 may be provided in the handle 12. The floss supply 38 may be packed into the handle in any desired manner, including loosely placed in the handle, wrapped around a horizontally positioned core, or wrapped around a vertically positioned core, such as that commercially available for use by dentists in table top floss dispensing apparatus. The preferred floss supply comprises a vertically positioned coreless spool of floss. Replacement spools are available in this form, allowing the flosser to be replenished and used indefinitely.

To remove the floss from the interior of the handle 12, an opening 40 is provided in the flosser through which an end of the floss can be threaded. Once on the exterior of the flosser 10, the floss 18 can then be threaded around the button 32, through the tines 16, and a second time around the button 32, as previously described. To aid in disposing of used floss, a cutting blade 44 is providing on the flosser 10. Ideally, the cutting blade 44 is positioned on the transition segment 14 or on the handle 12 in a manner that does not poise a threat to cutting the user's mouth or hand during use, as shown.

Figure 6:
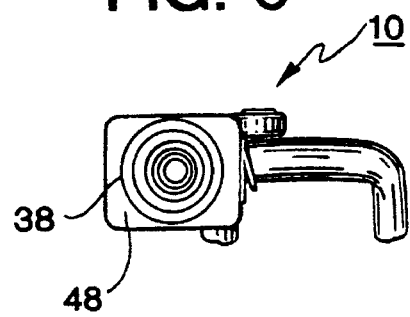
FIG. 6 is a bottom plan view of the floss holder of the present invention.

Another useful addition to the flosser of the present invention is providing some means for a user to readily determine how much floss is remaining in the flosser at any given time. Two such means are illustrated in this application. First, in FIG. 1, an opening or window 46 may be provided in the handle to permit viewing of the interior of the handle. Preferably, the window 46 is covered with a clear plastic or other transparent material that will protect the contents of the handle while allowing easy viewing. An alternative method of viewing the contents is shown in FIG. 6 whereby a transparent base 48 is employed that allows the floss supply 38 to be viewed from one end.

The flosser 10 of the present invention can be made from any suitable material, such as polypropylene, polycarbonate, acrylonitrile-butadiene-styrene, polystyrene, high impact polystyrene, glass reinforced polymers, acrylics, polyurethanes, etc. Preferably, the flosser is formed from an injection molded plastic material, such as polypropylene. Most preferably, the plastic material of which the floss holder was made contains an antimicobial or antibacterial additive which deters the growth of mildew, bacteria and germs on the floss holder. Most importantly, this property should be provided on the tines and in the area in which the floss spool is contained. This reduces the chance the floss may become contaminated in the bathroom environment which promotes the formation of these contaminates (e.g., antimicrobial activity such as staphylococcus aureus). The material may comprise:

1. a thermoplastic material and a 5–15% of an organic antimicrobial compound selected from aromatic acids, aromatic acid esters, and phenolic compounds;
2. a cation exchange polymer or a cation steriliser; and/or
3. a synthetic resin containing zinc oxide.

In the embodiment illustrated, the flosser is constructed from at least two pieces, joined together at seam 50. This allows easy insertion of the floss supply 38 by the manufacturer and, if not permanently sealed, allows the user to separate the flosser and replenish the floss supply as needed.

The flosser of the present invention is especially useful when it is employed to help manipulate new, highly slippery, flosses, such as that sold under the trademark GLIDE® by W. L. Gore & Associates, Inc., Flagstaff, Ariz. GLIDE floss comprises a strand of polytetrafluoroethylene (PTFE) that is quite slippery and which slides readily between a user's teeth. Unfortunately, this kind of floss also can be more difficult to handle then conventional nylon flosses. A flosser such as that taught in the present application may make the use of such highly slippery flosses much more convenient.

Figure 7:
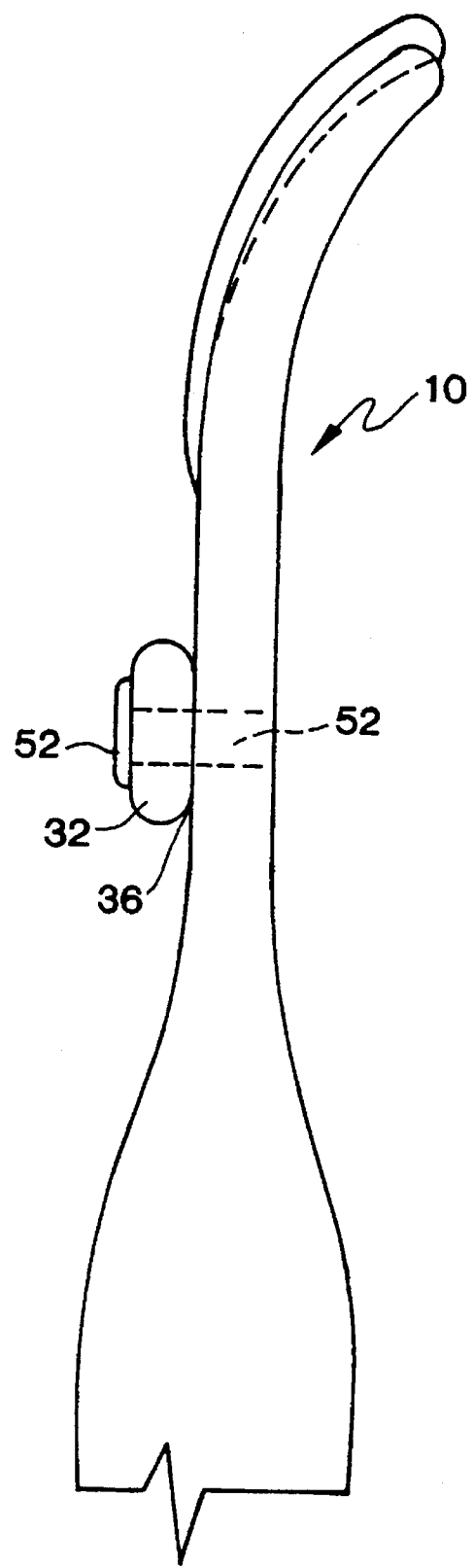
FIG. 7 is a side view of a flosser of the present invention illustrating a preferred button attachment mechanism.

One problem that has emerged with the use of PTFE flosses is that the floss may not readily attach around plain injection molded floss anchoring devices on the flosser of the present invention. FIG. 7 shows another embodiment of a button 32 anchoring device of the present invention that is particularly suitable for use with highly slippery floss products. In this instance, the button 32 is attached to the flosser 10 through the use of a rivet 52. The rivet 52 causes the button 32 to be held in extremely tight contact to the flosser 10, providing an especially constricted stem 36 for floss connection. Most preferably, the stem area between the button 32 and the flosser 10 is convexed in a manner to provide a tight "pinch point" for the floss. This attachment method has been demonstrated to produce a much better floss-around-floss attachment at the button, assuring a much more secure anchorage than glued, injection molded, or ultrasonically welded buttons.

The flosser of the present invention can be easily handled and manipulated. In order to reach top or bottom teeth on either side of the mouth, the flosser can be easily inverted. The angled orientation of the ends of the tines assists access to molar teeth. At all times, however, the offset nature of the tines assures a relatively unobscured view of the mouth during flossing.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A flosser device for use in holding a length of floss comprising a handle having a longitudinal axis, a pair of tines, and a transition segment attaching the pair of tines to the handle;

the pair of tines comprising a forked configuration so as to position a length of floss attached between the tines perpendicular to the longitudinal axis of the handle;

the transition segment between the handle and the pair of tines comprising a double bend between the handle and the pair of tines said double bend lying in a plane of said longitudinal axis so as to offset both of the tines to one side of the longitudinal axis of the handle.

2. The flosser device of claim 1 wherein the handle is hollow with a supply of floss provided therein; and the flosser includes at least one opening allowing floss to be threaded from the handle to the tines.

3. The flosser device of claim 2 wherein at least one button attached to the flosser, whereby floss is threaded through the opening, wrapped around the button, attached between the pair of tines, and wrapped a second time around the button to hold the floss taut between the tines.

4. The flosser device of claim 2 wherein a cutting blade is attached to the handle to allow floss to be cut and removed from the flosser after use.

5. The flosser device of claim 2 wherein the flosser includes a base on a distal end of the handle to allow the flosser to be stood upright on its distal end;

the base being slanted to lean the flosser toward a side opposite the side of the axis of the handle where the pair of tines are offset.

6. The flosser device of claim 5 wherein the base is transparent, allowing ready view of the floss remaining within the handle.

7. The flosser device of claim 2 wherein handle includes a transparent window therein to allow ready viewing of the floss remaining within the handle.

8. The flosser device of claim 1 wherein at least one button attached to the flosser, whereby floss is wrapped around the button, attached between the pair of tines, and wrapped a second time around the button to hold the floss taut between the tines.

9. The flosser device of claim 1 wherein the flosser includes an antimicrobial agent to avoid microbial growth thereon.

10. A flosser device for use in holding a length of floss comprising a handle having a longitudinal axis, a pair of tines, a transition segment attaching the pair of tines to the handle, and a base on a distal end of the handle;

the pair of tines comprising a forked configuration so as to position a length of floss attached between the tines perpendicular to the longitudinal axis of the handle;

the transition segment comprising a double bend between the handle and the pair of tines so as to offset both of the tines to one side of the longitudinal axis of the handle;

the base being slanted to lean the flosser toward a side opposite the side of the axis of the handle where the pair of tines are offset to allow the flosser to be stood upright on its distal end.

11. The flosser device of claim 10 wherein the handle is hollow with a supply of floss provided therein; and the flosser includes at least one opening allowing floss to be threaded from the handle to the tines.

12. The flosser device of claim 11 wherein a single button is attached to the flosser, whereby floss is threaded through the opening, wrapped around the button, attached between the pair of tines, and wrapped a second time around the button to hold the floss taut between the tines.

13. The flosser device of claim 12 wherein the floss contained in the flosser comprises a PTFE; and the button is riveted to the flosser to provide a tight constricted stem to securely retain the PTFE floss.

14. The flosser device of claim 10 wherein handle includes a transparent window therein to allow ready viewing of the floss remaining within the handle.

15. The flosser device of claim 14 wherein the transparent window comprises the base being transparent.

16. The flosser device of claim 10 wherein the flosser includes an antimicrobial agent to avoid microbial growth thereon.

* * * * *